US010444316B2

United States Patent
Greiser (10) Patent No.: US 10,444,316 B2
(45) Date of Patent: Oct. 15, 2019

(54) REDUCTION OF EDDY CURRENTS DURING FLOW ENCODED MAGNETIC RESONANCE IMAGING

(71) Applicant: Siemens Healthcare GmbH, Erlangen (DE)

(72) Inventor: Andreas Greiser, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 196 days.

(21) Appl. No.: 15/636,928

(22) Filed: Jun. 29, 2017

(65) Prior Publication Data

US 2018/0011160 A1 Jan. 11, 2018

(30) Foreign Application Priority Data

Jul. 5, 2016 (DE) .................. 102016212219 U (51) Int. Cl.
| | | |
|---|---|---|
| *G01R 33/565* | (2006.01) | |
| *G01R 33/48* | (2006.01) | |
| *G01R 33/561* | (2006.01) | |
| *G01R 33/563* | (2006.01) | |
| *A61B 5/055* | (2006.01) | |

(52) U.S. Cl.
CPC ... *G01R 33/56518* (2013.01); *G01R 33/4818* (2013.01); *G01R 33/5611* (2013.01); *G01R 33/56316* (2013.01); *A61B 5/055* (2013.01)

(58) Field of Classification Search
None
See application file for complete search history.

(56) References Cited

U.S. PATENT DOCUMENTS

2012/0076380 A1* 3/2012 Guhring ............... A61B 5/0263
382/131
2012/0223713 A1 9/2012 Greiser

FOREIGN PATENT DOCUMENTS

DE 4442086 A1 6/1995

* cited by examiner

*Primary Examiner* — Jermele M Hollington
*Assistant Examiner* — Douglas X Rodriguez
(74) *Attorney, Agent, or Firm* — Schiff Hardin LLP (57) ABSTRACT

In a method and magnetic resonance (MR) apparatus for establishing imaging sequence parameter values with a reduced eddy current formation for flow-encoded magnetic resonance imaging, a number of different flow-encoded candidate raw datasets are acquired by executing a flow-encoded gradient measurement sequence with different imaging sequence parameter values from a test or calibration region of an examination object. Flow-encoded candidate image datasets are reconstructed from the different flow-encoded candidate raw datasets. A flow-encoded candidate image dataset is selected as a function of a background phase contrast established in a phase-contrast image assigned to the respective flow-encoded candidate image dataset. The imaging sequence parameter values assigned to the flow-encoded candidate image dataset are selected as parameter values for an imaging sequence for subsequent diagnostic flow-encoded magnetic resonance imaging.

12 Claims, 3 Drawing Sheets

REDUCTION OF EDDY CURRENTS DURING FLOW ENCODED MAGNETIC RESONANCE IMAGING

BACKGROUND OF THE INVENTION

Field of the Invention

The invention concerns a method for establishing imaging parameters with a reduced formation of eddy currents for flow-weighted magnetic resonance imaging. Furthermore the invention concerns a method for acquisition of flow-weighted magnetic resonance image data. In addition the invention concerns a control computer for a magnetic resonance system, and a magnetic resonance system, that implement such methods.

Description of the Prior Art

Magnetic resonance recordings are to be understood below as image data created from within an examination object by the operation of a magnetic resonance scanner that is activated within the framework of the method, but also as parameter maps which reproduce a spatial or temporal distribution of specific parameter values within the examination object, and which can be created from the image data, for example.

MR phase-contrast flow imaging (also referred to as flow-weighted magnetic resonance imaging, phase-contrast flow measurement, phase-contrast imaging, phase-contrast measurement or flow-encoded magnetic resonance imaging) is a non-invasive, quantitative method able to be used in vivo. Phase-contrast flow measurement is based on the different phases, which can develop during an MR recording in the transversal magnetization. In the presence of gradient fields that vary over time, a magnetization moved in the external $B_0$-field picks up a phase. This can be used to encode velocities. To this end the different influences of the MR imaging on the magnetization are compensated by specific gradient switchings such that only phase differences that are formed as a result of the movement of the magnetization still remain, for example during the flow of the blood in a vessel relative to the stationary vessel wall. Expressed in different terms, the magnetization of the flowing material, through the application of a bipolar gradient, obtains a phase offset that is proportional to the velocity of the flowing particles. Stationary examination regions ideally do not exhibit this phase. The phase information of an MR signal is contained in the phase of the signal, which is usually discarded in conventional MR measurements, or is computed with the actual anatomical magnitude image. Under normal circumstances the phase of the signal does not contain any meaningful, usable information. However, in phase-contrast measurement, the phase information is reconstructed into a phase image as its own dataset. This phase image contains, encoded as a gray scale in each pixel, information about the velocity and direction of the corresponding pixel or image voxel. The direction is encoded as a gray level scale. With white pixels the flow is directed toward the observer, with black pixels the flow is directed away from the observer.

For the creation of flow-encoded magnetic resonance recordings flow-encoded raw data must first be acquired. This is done with specific measurement sequences, which are referred to below as phase-contrast measurement sequences. Subsequently a reconstruction of flow-encoded magnetic resonance image data is undertaken, using a Fourier transformation, for example.

During phase-contrast flow measurement various noise phenomena occur, which can adversely affect the result. One phenomenon is known as phase convolution, or aliasing that is attributable thereto. This originates from the fact that only values of the phase of the transverse magnetization from +180° to −180° can be correctly recognized. All values that exceed these figures are not correctly recognized and are incorrectly represented as flows in the opposite direction in the dataset or in the phase image. Therefore, before a phase-contrast measurement, the velocity range of the region to be examined or of the fluids moving therein must be defined. In such cases the gradient profile of the sequence is modified so that the maximum phase difference of +/−180° just corresponds to the specified velocity range. This velocity is referred to as the encoding velocity (VENC). Values of the VENC that are too low lead to the aliasing already mentioned. Moreover, the noise of a phase-contrast flow measurement increases with the level of the VENC so that, with a VENC that is selected with too high a value, a falsification of the measurement results is likewise to be expected.

Unfortunately, eddy current fields can be caused by the flow-encoding gradients, which lead to image distortions, the appearance of which depends both on the amplitude of the gradients and on their direction. If the individual images recorded are then combined with one another without correction, in order to create the parameter maps for example, the various distortions lead to incorrect assignments of pixel information and thus to errors, or at least to a reduced precision of the computed parameters.

The aforementioned eddy current fields, also referred to as eddy currents, occur during the measurement due to currents induced in the conducting parts of the magnet housing by the switching of the gradient magnetic fields. While the eddy current fields that occur during the phase-contrast imaging of isolated gradient trains with longer time constants can be reduced by suitable compensation procedures, with fast imaging sequences with short repetition rates of the gradient trains, a pseudo-steady-state eddy current effect occurs, which is complex to describe with a model and thus is also difficult to compensate. In the case of phase-contrast flow measurements, this effect can amount to several percent of the measured value and thus contribute to accuracy requirements not being achieved. This means that the information content of the results of the phase-contrast flow measurements is adversely affected.

The phase errors occurring as a result of the eddy current fields can be excluded from the measurements for example, depending on their location, with the use of an additional phantom measurement, and can be separated in this way from the actual flow velocity information. Also, based on image regions in which only stationary tissue is present, a model function can be adapted to measured values of background phases and in this way information with respect to the background phase values in the regions in which a phase contrast occurs can be obtained. A further approach based on a model is the modeled establishment of a response function of the gradient system as a function of any given gradient form, which is also referred to as GIRF formation.

All these methods are based on assumptions made about the characteristics of the eddy current fields, and the phase-contrast images are corrected retrospectively with the corresponding physical and method-specific restrictions.

SUMMARY OF THE INVENTION

An object of the present invention is to provide a method with reduced eddy current formation for flow-encoded magnetic resonance imaging.

In the inventive method for establishing imaging sequence parameter values with a reduced eddy current formation for flow-encoded magnetic resonance imaging, in a preliminary recording, a number of different flow-encoded candidate raw datasets are acquired by the execution of a flow gradient measurement sequence with different imaging sequence parameter values from a test or calibration region of an examination object. A preliminary recording in this context means an MR data acquisition that is not the actual diagnostic flow-encoded imaging of the examination object, which will be used later for an analysis, evaluation or diagnosis. Preliminary recording can mean, for example, that the preliminary recording is carried out entirely before the actual image recording. However an image recording at intervals can also be selected, in which, in each time interval, first a preliminary recording is carried out and subsequently in each case a time segment with the actual image recording sequence follows (interleaved recordings). The test or calibration region can be, for example, a sub-region of a region to be recorded later with the actual image recording, or the entire imaging region of the examination object to be recorded later. As an alternative the test or calibration region can lie outside an imaging region to be recorded later. Values of parameters of a pulse sequence for flow-encoded magnetic resonance imaging should be understood as imaging sequence parameter values in this context.

A variation of parameters of a flow-encoded measurement sequence thus takes place within the framework of the preliminary recording. On the basis of the different flow-encoded candidate raw datasets flow-encoded candidate image datasets are reconstructed. Such a reconstruction can, as is usual, be based on a Fourier transformation of the k-space data into the image data domain. Subsequently a flow-encoded candidate image dataset is selected as a function of an established background phase contrast in a phase-contrast image assigned to the respective flow-encoded candidate image dataset. In accordance with the invention, the observation that different imaging sequence parameter values also cause different background phase contrasts is used. In such cases it is important to take account of the fact that specific parameters, such as the echo time or the repetition time, can be changed only within certain boundaries. For example an echo time that is too long would result in significant signal losses. The invention is based on the insight that even a small change to one or another of the imaging sequence parameter values by a few percent has a serious effect on the background phase contrast. Background phase contrast in this context should be considered as a phase-contrast signal occurring in a stationary image region, i.e. in an image region without spins in motion, which can occur for example because of eddy currents.

Finally the imaging sequence parameter values assigned to the selected flow-encoded candidate image dataset are selected as parameter values for an imaging sequence for subsequent flow-encoded magnetic resonance imaging.

Thus the imaging sequence parameter values are advantageously set even before the flow-encoded magnetic resonance imaging such that noise effects, as a result of eddy current fields for example, are reduced and in the best case are minimal. The method of operation can be implemented without a model and thus flexibly and without any processing effort. The preliminary recording, apart from the aforementioned variations, preferably has the same timing, the same slice orientation and the same flow-encoding gradient trains as the later diagnostic measurement, to which the parameters established are transferred, so the effect of the eddy current fields established in the preliminary recording is able to be transferred to the actual flow contrast measurement.

The inventive method for acquisition of flow-encoded magnetic resonance image data uses a preliminary recording as a test, so as to establish imaging sequence parameter values with a reduced eddy current formation for the flow-encoded magnetic resonance imaging. Subsequently, within the framework of magnetic resonance imaging, flow-encoded raw data are acquired by the execution of a flow gradient measurement sequence with the defined imaging sequence parameter values from a region of an examination object that is to be diagnostically evaluated. Finally flow-encoded image data are reconstructed on the basis of the acquired flow-encoded raw data.

An inventive control computer for a magnetic resonance system has a radio-frequency transmission system for producing signals that are provided to an RF transmit antenna that cause radio-frequency pulses to be radiated by the RF transmit antenna of the magnetic resonance scanner, and a gradient system interface for activating gradient coils of the magnetic resonance scanner. Furthermore the inventive control computer has a radio-frequency reception system that receives raw data via one or more RF reception antennas of the magnetic resonance scanner. A sequence controller is also part of the inventive control computer, which, for a preliminary recording as a test for creation of diagnostic magnetic resonance recordings of an examination object, sends sequence control data with different imaging sequence parameter values to the radio-frequency transmission system, the gradient system interface, and the radio-frequency reception system, so that a number of different flow-encoded candidate raw datasets are acquired by the execution of a flow gradient measurement sequence with different imaging sequence parameter values from a test or calibration region of an examination object. The inventive control computer has an image reconstruction processor that reconstructs flow-encoded candidate image datasets on the basis of the different flow-encoded candidate raw datasets, and a selection processor that selects a flow-encoded candidate image dataset as a function of a background phase contrast established in a phase-contrast image assigned to the respective flow-encoded candidate image dataset. In addition, the inventive control computer has a definition processor that defines the imaging sequence parameter values assigned to the selected flow-encoded candidate image dataset as parameter values for an imaging sequence for subsequent flow-encoded magnetic resonance imaging.

An inventive magnetic resonance apparatus has a data acquisition scanner that has a basic field magnet, which produces a basic magnetic field in the conventional way in a patient measurement volume of the scanner, and a transmit antenna system as described above, a gradient system having a number of gradient coils, a receive antenna system, and an inventive control computer as described above.

In particular the sequence controller, the image reconstruction processor, the selection processor and the definition processor of the inventive control computer are preferably realized in the form of software of a suitable programmable control computer with corresponding storage options. Also the radio-frequency transmit system, the gradient system interface, and the radio-frequency receive system can be realized at least partly in the form of software, wherein once again other units of these components are pure hardware units, for example the radio-frequency amplifiers, the radio-frequency transmitter, a gradient pulse generator of the gradient system interface, or an analog/digital converter of the radio-frequency receive system, etc. A largely software realization, in particular of the aforementioned components, has the advantage that magnetic resonance system control computers already in existence can be upgraded in a simple manner by a software update, in order to operate in the inventive way.

For this purpose, the present invention also encompasses a non-transitory, computer-readable data storage medium encoded with programming instructions, the storage medium being loaded into a computer system of a magnetic resonance apparatus, the program code causing one or more of the embodiments of the inventive method described above to be implemented when the program code is executed by the computer system.

Such a storage medium can, as needed, also include additional elements such as e.g. documentation and/or additional components, also hardware components, such as e.g. hardware keys (dongles etc.) for use of the software.

The computer-readable medium can be, for example, a memory stick, a hard disk or another transportable or built-in data carrier, on which the program code is read in and executed by a processing unit of the control stored.

In a preferred embodiment of the inventive method for establishing imaging sequence parameter values with a reduced eddy current formation for flow-encoded magnetic resonance imaging, in the selection step, a flow-encoded candidate image dataset is selected for which the assigned phase-contrast image exhibits the weakest background phase contrast in the part region. The insight that a local minimum relating to the background phase contrast exists in an interval, which describes a possible variation of imaging sequence parameter values, for example by a few percent, is used to advantage. This local minimum is at least approached by selection of the flow-encoded candidate image dataset with the weakest background phase contrast. The assessment as to whether the background phase contrast is minimized can be made by observing the individual images. In such cases a sufficiently stationary signal must be present in the imaging slice for the visual evaluation to function reliably. If necessary additional signal sources, such as bottles with liquid or gel cushions, can be introduced into the examined test or calibration region.

An average value over a phase contrast in the examined part region can be used as the background contrast to be minimized. In this way, information about a greater surface area is taken into account, which, with a certain variation of the background phase contrast as a function of the location, delivers a more representative result.

In another embodiment of the inventive method, a region of the examination object with a stationary phase signal is established or sought as the test or calibration region. This means a region is selected in which no organ movement and no flow movement are taking place. If the inventive method is used, for example, to prepare for displaying an image within the framework of angiography imaging, then a region outside the heart, for example the edge of the chest or similar, is used as the test or calibration region. In this way, during the establishment of the imaging sequence parameter values, only phase signals emanating from noise effects are considered, which are actually to be reduced or minimized as much as possible.

Preferably an overall phase error is thus minimized as the sum of the phase errors of the test or calibration region, so that a spatial dependence of the background phase no longer plays a role. I.e. the phase errors are minimized on a ring around the isocenter, so that this also applies with high probability to the region within the ring, in which the structures to be imaged, such as vessels, lie.

The test or calibration region with a stationary phase signal is preferably established in an automated manner. The test or calibration region can be realized, for example, with the use of an algorithm on the basis of a phase-contrast measurement, with which pixels are identified in an image region to be recorded later, which exhibit a stationary phase signal, which indicates that no movement or no change in movement occurs at these points.

The selected test or calibration region can, but does not have to be, a sub-region of a region of the examination object to be imaged subsequently. Thus, sub-regions of a region with a stationary phase signal to be imaged subsequently with the use of a phase-contrast imaging method are identified. Advantageously, it can be assumed in this case that the noise effects of adjacent image regions do not differ significantly from one another, so that it can be assumed that a minimization of the established background phase signal in the part region of the region to be imaged also causes an at least approximate minimization of the background phase signal in regions with a dynamic phase signal.

In an embodiment of the inventive method, the varied imaging sequence parameter values relate to one of the following parameters:

a first gradient moment of the flow-encoding gradients, and/or higher gradient moments, a precise course of the flow-encoding gradients, a slice orientation and the orientation of the flow-encoding gradients associated therewith, an echo time, a repetition time.

Thus, depending on specific requirements and restrictions of a measurement sequence, the respective parameters, which are either subject to especially low restrictions or for which a small change in the parameter value already leads to a marked reduction in the background phase contrast, can advantageously be varied. In this way an optimum reduction in the noise effects resulting from eddy current fields is achieved, wherein at the same time other requirements for image quality can be fulfilled, since the restrictions to be adhered to for said requirements in each case are adhered to for the individual parameter values.

A number of the aforementioned parameters can also be varied as a test, in order to establish a suitable set of imaging sequence parameter values. The variation of the imaging sequence parameter values can preferably be done by interactive changes during the run time of the preliminary recording or automated at predetermined time intervals as a so-called parameter sweep. In this way the selection process of the suitable imaging sequence parameter values can take place in a semi-automated or fully-automated manner, so that a user is relieved at least partly of selecting parameter values or even of appraising candidate images. With full automation users without any qualifications or experience can also be used in the selection of the suitable parameter values. Time for the appraisal of the candidate image datasets is also saved by a full automation. This is especially important and advantageous for example for a time limitation for the preliminary recording, the selection of the imaging sequence parameter values and the subsequent magnetic resonance imaging. If, for example, phase contrast imaging of the heart of a patient, while the patient is holding his or her breath, is to be carried out, then under some circumstances it is necessary for both the preliminary recording, the selection of the imaging sequence parameter values, as well as the subsequent magnetic resonance imaging, to have to be carried out during a time interval that corresponds to a period of time for which a patient is holding his or her breath. In this application it is thus especially important that the two first steps take as little time as possible, in order to have as much time as possible for the actual phase contrast magnetic resonance imaging. For example a breath-holding period can amount to around 15 seconds. Then a single preliminary recording with a predetermined set of imaging sequence parameter values can take around 100 ms. In this embodiment, around 20 different sets of imaging sequence parameter values can thus be tested in total in 2 seconds. Subsequently the test series is evaluated in around 5 seconds, so that there are still 8 seconds left for the actual phase-contrast imaging. Thus, with this method of operation, the preliminary recording can be integrated directly into the workflow of a dynamic phase-contrast imaging, without having to change the overall sequence or allow for a loss of time. The preliminary recording can thus advantageously be done in real time, so that the suitable imaging sequence parameters established therefrom correspond to the current situation in each case.

In a variant of the inventive method, a reduced spatial and/or temporal resolution is used for the acquisition of the flow-encoded candidate raw datasets. Thus the test-mode phase-contrast image recording can be realized with relatively little outlay in time and in this way can be integrated easily into a time-limited workflow. Subsequently the actual imaging is started with enhanced resolution.

In an especially easy to realize variant of the inventive method, the selection step is undertaken by visual appraisal of the phase-contrast images assigned to the respective flow-encoded candidate image datasets. In this variant an experienced user or an additional person appraises the acquired candidate images and selects those candidate image datasets that exhibit the characteristically weakest background phase contrast.

In an alternate variant of the inventive method, the selection step is undertaken by an automated establishment of a characteristic variable, for example an average value of a background phase contrast in the part region. This means the candidate image datasets are analyzed in this variant in an automated manner, wherein a characteristic variable is automatically established and compared in relation to the background phase contrast of the individual candidate image datasets. Advantageously with this variant, no time has to be expended for an appraisal of the candidate image datasets.

For quality assurance, limit values can also be defined for the background phase. It can be defined in advance, for example, that only candidate image datasets of which the background phase values do not exceed a specific limit value can be selected. If the limit values are not exceeded by any of the candidate image datasets, then for example the user can be notified in an automated manner that no sufficiently good result can be achieved for the selected parameter variation. It can be proposed automatically to the user for example that they vary another imaging sequence parameter or that they vary the same imaging sequence parameter in another range of values. Through these very flexible and interactive quality requirements can be fulfilled more easily or suitable compromises of the image quality can be found for the respective requirement.

DESCRIPTION OF THE PREFERRED EMBODIMENTS

Figure 1:
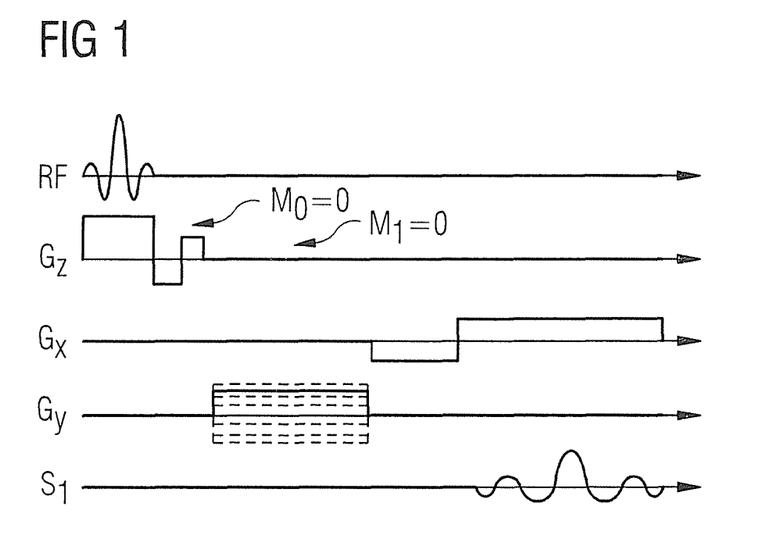
FIG. 1 shows a pulse diagram, which illustrates a test or calibration sequence as a reference measurement for flow-encoded magnetic resonance imaging.

FIG. 1 shows a pulse diagram, which illustrates a sequence for a reference measurement for flow-encoded magnetic resonance imaging. In a first line a radio-frequency excitation pulse RF is shown, with which spins are excited in a region to be examined. Simultaneously with the radio-frequency excitation pulse RF, a slice-selection gradient $G_z$ shown in the second line is also applied in the z-direction. The slice-selection gradient $G_z$ is designed so that its zero gradient moment $M_0$ and its first gradient moment $M_1$ each have the value 0. The zero gradient moment $M_0$ is produced as the integral of the slice-selection gradient $G_z$ over time:

$$M_0 = \int_0^t G_z(t')dt'. \qquad (1)$$

The first gradient moment $M_1$ is produced as the integral of the product of the slice-selection gradient $G_z$ and the location z(t) over time:

$$M_0 = \int_0^t z(t')G_z(t')dt'. \qquad (2)$$

The sequence shown in FIG. 1 can be used for a measurement of a reference phase, from which velocity-related phase values can be subtracted. A read-out gradient $G_x$ is shown in a third line in FIG. 1, with which a first magnetic resonance signal or read-out signal $S_1$ (see bottom line in FIG. 1) is read out. Also shown in FIG. 1 is a gradient $G_y$ in the phase-encoding direction, with which a non-velocity-dependent phase of a read-out signal is influenced.

Figure 2:
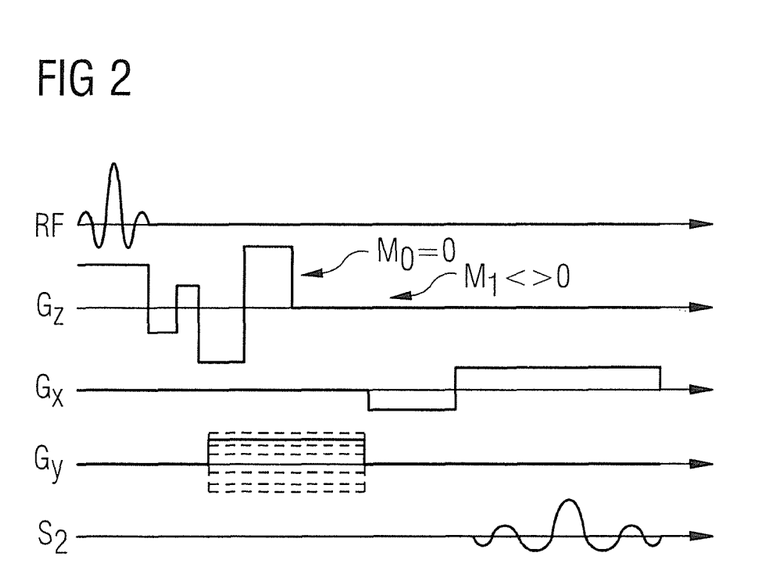
FIG. 2 shows a pulse diagram, which illustrates a sequence for measuring a velocity in the z-direction within the framework of diagnostic flow-encoded magnetic resonance imaging.

FIG. 2 shows a pulse diagram, which illustrates a sequence for a measurement for diagnostic flow-encoded magnetic resonance imaging. In a first line a radio-frequency excitation pulse RF is shown, with which spins are excited in a region to be examined. Simultaneously with the radio-frequency excitation pulse RF, a slice-selection gradient $G_z$ shown in the second line will also be applied in the z-direction. Unlike in the part sequence in FIG. 1, in FIG. 2 the slice-selection gradient $G_z$ is supplemented by a proportion, so that although the magnetic moment zero $M_0$ of the gradient $G_z$ has the value 0, as it does in the part sequence in FIG. 1, the first magnetic moment $M_1$ is not equal to 0 however.

For an excitation with this part sequence a phase of a second read-out signal $S_2$ with a velocity-dependent proportion is created, which can be measured as the phase of the second read-out signal $S_2$. By subtracting the phase of the first read-out signal $S_1$ established with the aid of the first part sequence from the phase of the second read-out signal $S_2$ established with the second part sequence, the velocity-dependent proportion of the signal phase in the z-direction, also referred to as the phase-contrast or flow contrast in the z-direction, is established. In a similar way the velocity-dependent phase signals in the x- and y-direction can also be measured, from which once again the stationary phase established with the first read-out signal $S_1$ must be subtracted. Basically velocity-dependent phase signals only occur in part regions of an examination region in which moving spins, i.e. moving material, is present, however as a result of the eddy current fields or eddy current described at the outset, phase-contrasts are also measured in regions without moving spins. In order to minimize this effect, a method for acquisition of flow-encoded magnetic resonance image data in accordance with an exemplary embodiment of the invention is shown in FIG. 3.

Figure 3:
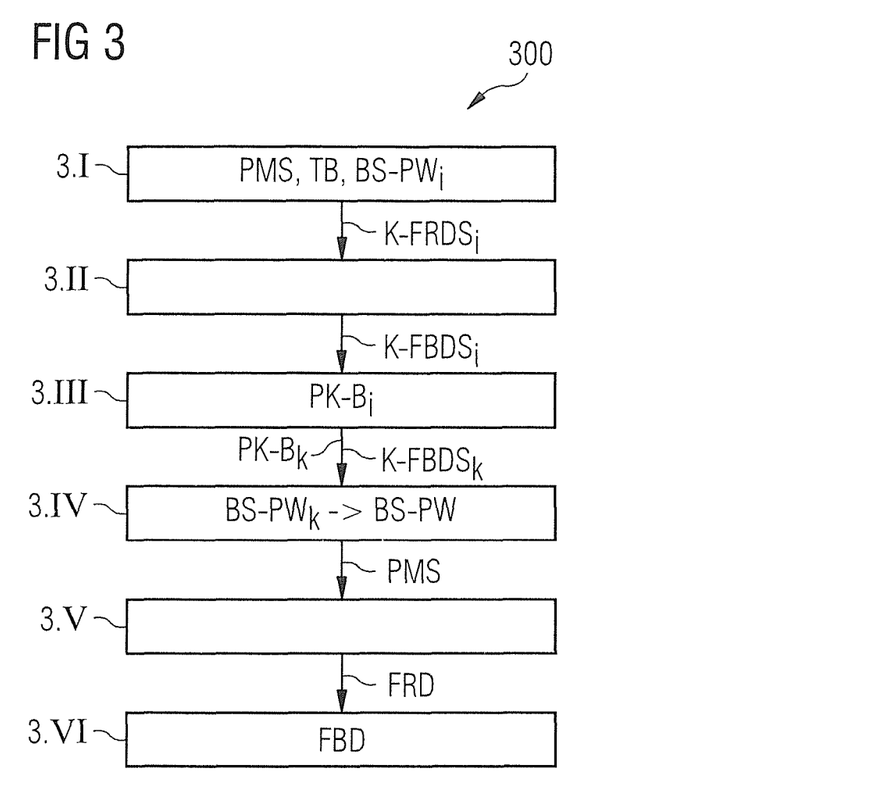
FIG. 3 shows a flowchart of the basic steps of a method for acquisition of flow-encoded magnetic resonance image data in accordance with an exemplary embodiment of the invention.

FIG. 3 shows a flowchart 300 with the basic steps of such a method for acquisition of flow-encoded magnetic resonance image data. In a step 3.I, in a test-mode recording, also known as a preliminary recording, first of all a number of different flow-encoded candidate raw datasets K-FRDS$_i$ are acquired with the aid of a phase-contrast measurement sequence PMS with different imaging sequence parameter values BS-PW$_i$ from a part region TB of an examination object O. In this case the part region TB is preferably selected so that above all stationary tissue, in which no moving spins are present, is present in the part region.

To this end individual parameters, such as the echo time, the repetition time of the sequence PMS or the gradient form of the respective flow-encoding gradients, are varied between the recording of the individual candidate raw datasets K-FRDS$_i$. Depending on the variation of the parameters, the effects created as a result of the eddy current fields on the phase signals are characterized differently. In order to establish these effects, in a step 3.II, flow-encoded candidate image datasets K-FBDS$_i$ are reconstructed on the basis of the different flow-encoded candidate raw datasets K-FRDS$_i$. The reconstruction is done with a usual reconstruction method for reconstruction of image data, which is based on a Fourier transformation for example. Subsequently, in a step 3.III, the phase-contrast images PK-B$_i$ assigned to the reconstructed flow-encoded candidate image datasets K-FBDS$_i$ are examined and compared in respect of a characterization of the eddy-current-related phase contrast. Preferably the phase-contrast image PK-B$_k$ or the associated phase-contrast image dataset K-FBDS$_k$ is now established, for which the lowest eddy-current-related phase contrast occurs. Subsequently, in a step 3.IV, the imaging sequence parameter values BS-PW$_k$ assigned to the phase-contrast image PK-B$_k$ established is defined as parameter values BS-PW for subsequent flow-encoded magnetic resonance imaging.

In a step 3.V the actual flow-encoded magnetic resonance imaging, for example of a heart in motion, is started. Here the flow-encoded raw data FRD is acquired with the aid of a phase-contrast measurement sequence BS with the defined imaging sequence parameter values BS-PW from a region of an examination object O to be examined, in this case, the heart of a patient. Finally, in a step 3.VI, flow-encoded image data FBD are reconstructed on the basis of the acquired flow-encoded raw data FRD. Artifacts resulting from eddy current fields are minimized in the images created on the basis of the flow-encoded image data FBD.

Figure 4:
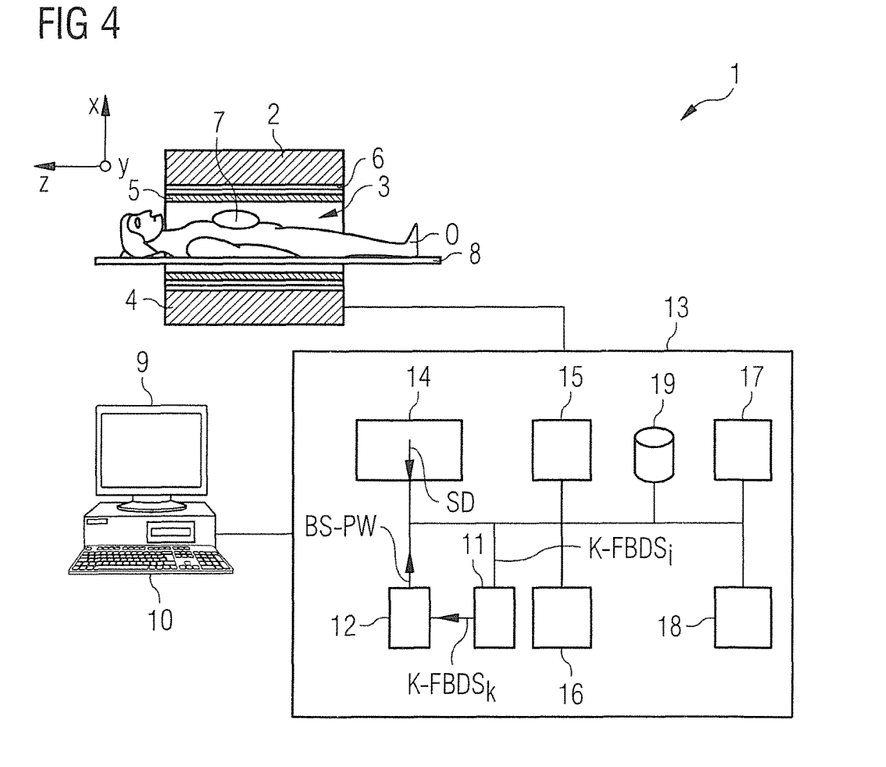
FIG. 4 is a schematic illustration of a magnetic resonance apparatus in accordance with an exemplary embodiment of the invention.

FIG. 4 shows a schematic illustration of an inventive magnetic resonance system 1 (abbreviated below to "MR system"), which has a control computer 13 in accordance with an exemplary embodiment of the invention. The magnetic resonance system includes the actual magnetic resonance scanner 2 with an examination volume 3 or patient tunnel, into which an examination object O (a patient or test subject) in which the examination object, for example a specific organ, is located, can be moved on a bed 8.

The magnetic resonance scanner 2 is equipped in the usual way with a basic field magnet 4, a gradient system 6 and an RF transmit antenna system 5 and an RF receive antenna system 7. In the exemplary embodiment, the RF transmit antenna system 5 involves a whole-body coil permanently installed in the magnetic resonance scanner 2, while the RF receive antenna system 7 includes local coils to be arranged on the patient or test subject (symbolized in FIG. 4 by just one single local coil). Basically, the whole-body coil can also be used as the RF receive antenna system and the local coils can be used as the RF transmit antenna system, provided these coils are able to be switched in different operating modes in each case.

The MR system 1 also has the central control computer 13 already mentioned in accordance with an exemplary embodiment of the invention, which is used for controlling the MR system 1. This central control computer 13 has a sequence controller 14 for pulse sequence control. The sequence of radio-frequency pulses (RF pulses) and of gradient pulses is controlled by this unit as a function of a selected imaging sequence. Such an imaging sequence can be predetermined, for example, within a measurement or control protocol. Usually different control protocols are stored in a memory 19 for different measurements and can be selected by a user (and where necessary changed if required) and can then be used for carrying out the measurement.

For output of the individual RF pulses, the central control computer 13 has a radio-frequency transmit system 15, which creates the RF pulses, amplifies them and injects them via a suitable interface (not shown in detail) into the RF transmit antenna system 5. For control of the gradient coils of the gradient system 6, the control computer 13 has a gradient system interface 16. The sequence controller 14 communicates with the radio-frequency transmit system 15 in a suitable way, e.g. by sending out sequence control data SD, and with the gradient system interface 16 for sending out the pulse sequences. The control computer 13 also has a radio-frequency receive system 17 (likewise communicating in a suitable way with the sequence controller 14), in order to acquire magnetic resonance signals, i.e. raw data, received in a coordinated manner from the RF transmit antenna system 7.

A reconstruction processor 18 accepts the acquired raw data and reconstructs the MR image data therefrom. This image data can then be stored in a memory 19 for example and/or can be further processed, in order to establish optimum imaging parameters BD-PW for phase-contrast imaging in accordance with the method described in conjunction with FIG. 3. To this end reconstructed, flow-encoded candidate image datasets K-FBDS$_i$ are transferred to a selection unit 11, which selects from the flow-encoded candidate image datasets K-FBDS$_i$ that have been reconstructed by the reconstruction processor 18 on the basis of acquired flow-encoded candidate-raw data, a suitable or an optimal flow-encoded candidate image dataset K-FBDS$_k$. Then, in a definition processor 12—as has already been explained—the imaging sequence parameter values BS-PW assigned to the selected flow-encoded candidate image dataset K-FBDS$_k$ are defined as imaging sequence parameter values BS-PW for a subsequent magnetic resonance image recording of the patient O and transferred to the sequence controller 14 or transferred for storage to the memory 19.

As an alternative, the selection processor 11 can be integrated into the reconstruction processor 18 here or can be linked externally via a network or the like to the central control computer 13.

The central controller 13 can be operated via a terminal with an input unit 10 and a display unit 9, with which the entire MR system 1 can also be operated by an operator. MR images can also be displayed on the display unit 9 and during the selection step can be appraised by a user, and by means of the input unit 10, if necessary in combination with the display unit 9, measurements can be planned and started and in particular suitable control protocols with suitable measurement sequences, as explained above, can be selected and modified if necessary.

Moreover, the inventive MR system 1 and in particular the control computer 13 can have a number of further components, not shown individually here but usually present in such devices, such as a network interface for example, in order to connect the overall system to a network and to be able to exchange raw data and/or also further data, such as patient-relevant data or control protocols, for example.

How suitable raw data can be acquired by radiating RF pulses and creating gradient fields and how MR images can be reconstructed from the raw data are basically known to those skilled in the art and need not be explained in greater detail herein. Likewise the principles of a wide range of measurement sequences, such as EPI measurement sequences or measurement sequences for creating flow-encoded images, are known to those skilled in the art.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for establishing imaging sequence parameter values that operate a magnetic resonance (MR) data acquisition scanner with a reduced eddy current formation for flow-encoded MR imaging, said method comprising:

operating said MR data acquisition scanner to execute a plurality of flow-encoded gradient measurement sequences, respectively with different imaging sequence parameter values, in order to acquire a plurality of different flow-encoded candidate raw datasets from a test or calibration region of an examination object in the MR data acquisition scanner;

providing said different flow-encoded candidate raw datasets to a reconstruction processor and, in said reconstruction processor, reconstructing flow-encoded candidate image datasets respectively from said different flow-encoded candidate raw datasets, with each of said flow-encoded candidate image datasets having a respective phase-contrast image assigned thereto;

in a selection processor, selecting a flow-encoded candidate image dataset, from among said flow-encoded candidate image datasets, for which the phase-contrast image assigned thereto exhibits a lowest background phase contrast in said test or calibration region; and in a defining processor, defining imaging sequence parameter values assigned to the selected flow-encoded candidate image dataset, as parameter values for subsequent execution of a diagnostic flow-encoded gradient MR sequence, and providing said parameter values for said diagnostic flow-encoded gradient MR sequence in an electronic form configured to operate said MR data acquisition scanner.

2. A method as claimed in claim 1 comprising using a region of the examination object having a stationary phase signal as said test or calibration region.

3. A method as claimed in claim 2 comprising, in said selection processor, identifying said test or candidate region having a stationary phase signal automatically.

4. A method as claimed in claim 1 comprising receiving a manual entry into said selection processor that establishes said test or candidate region.

5. A method as claimed in claim 1 comprising generating said image sequence parameter values from the group consisting of a first gradient moment of flow-encoded gradients, gradient moments higher than the first gradient moment of the flow-encoded gradients, a course of flow-encoded gradients, a slice orientation from which flow-encoded MR data are to be acquired, an echo time at which MR signals are read out in said flow-encoded gradient MR sequence, and a repetition time of said flow-encoded gradient MR sequence.

6. A method as claimed in claim 1 comprising operating said MR data acquisition scanner to acquire said flow-encoded candidate raw datasets with at least one of a spatial resolution or a temporal resolution that is lower than a spatial resolution or a temporal resolution in said diagnostic flow-encoded gradient MR sequence.

7. A method as claimed in claim 1 comprising displaying the phase-contrast images assigned to the respective flow-encoded candidate image datasets at a display in communication with said selection processor, and selecting the selected flow-encoded candidate image dataset dependent on a manual entry made in selection processor after a visual evaluation of the displayed phase-contrast images.

8. A method as claimed in claim 1 comprising selecting the selected flow-encoded image dataset for which an average value of the background phase contrast in said test or calibration region is lowest.

9. A method as claimed in claim 1 comprising:

operating the MR data acquisition scanner to execute said diagnostic flow-encoded gradient MR sequence to acquire diagnostic flow-encoded raw data from a diagnostic region of the examination object; and providing the diagnostic flow-encoded raw data to said reconstruction processor and, in said reconstruction processor, reconstructing diagnostic flow-encoded image data from the acquired diagnostic flow-encoded raw data, and making the reconstructed diagnostic flow-encoded image data available from the reconstruction computer in electronic form as a data file.

10. A magnetic resonance (MR) apparatus comprising:

an MR data acquisition scanner;

a control computer configured to operate said MR data acquisition scanner to execute a plurality of flow-encoded gradient measurement sequences, respectively with different imaging sequence parameter values, in order to acquire a plurality of different flow-encoded candidate raw datasets from a test or calibration region of an examination object in the MR data acquisition scanner;

a reconstruction processor provided with said different flow-encoded candidate raw datasets, said processor being configured to reconstruct flow-encoded candidate image datasets respectively from said different flow-encoded candidate raw datasets, with each of said flow-encoded candidate image datasets having a respective phase-contrast image assigned thereto;

a selection processor configured to select a flow-encoded candidate image dataset, from among said flow-encoded candidate image datasets, for which the phase-contrast image assigned thereto exhibits a lowest background phase contrast in said test or calibration region; and a defining processor configured to define imaging sequence parameter values assigned to the selected flow-encoded candidate image dataset, as parameter values for subsequent execution of a diagnostic flow-encoded magnetic resonance imaging, and to provide said parameter values for said diagnostic flow-encoded magnetic resonance imaging in an electronic form configured to operate said MR data acquisition scanner.

11. A method for establishing imaging sequence parameter values that operate a magnetic resonance (MR) data acquisition scanner with a reduced eddy current formation for flow-encoded MR imaging, said method comprising:

operating said MR data acquisition scanner to execute a plurality of flow-encoded gradient measurement sequences, respectively with different imaging sequence parameter values, in order to acquire a plurality of different flow-encoded candidate raw datasets from a test or calibration region of an examination object in the MR data acquisition scanner, each of said flow-encoded candidate raw datasets having a spatial resolution and a temporal resolution, with at least one of the spatial resolution and the temporal resolution being lower than a spatial resolution and a temporal resolution in a diagnostic flow-encoded gradient MR sequence that is to be subsequently executed;

providing said different flow-encoded candidate raw datasets to a reconstruction processor and, in said reconstruction processor, reconstructing flow-encoded image datasets respectively from said different flow-encoded candidate raw datasets;

in a selection processor, selecting a flow-encoded candidate image dataset, from among said flow-encoded candidate image datasets, dependent on a background phase contrast established in a phase-contrast image assigned to one of said flow-encoded candidate image datasets; and in a defining processor, defining imaging sequence parameter values assigned to the selected flow-encoded candidate image dataset, as parameter values for said subsequent execution of said diagnostic flow-encoded gradient MR sequence, and providing said parameter values for said diagnostic flow-encoded gradient MR sequence in an electronic form configured to operate said MR data acquisition scanner.

12. A magnetic resonance (MR) apparatus comprising:

an MR data acquisition scanner;

a control computer configured to operate said MR data acquisition scanner to execute a plurality of flow-encoded gradient measurement sequences, respectively with different imaging sequence parameter values, in order to acquire a plurality of different flow-encoded candidate raw datasets from a test or calibration region of an examination object in the MR data acquisition scanner, each of said flow-encoded candidate raw datasets having a spatial resolution and a temporal resolution, with at least one of the spatial resolution and the temporal resolution being lower than a spatial resolution and a temporal resolution in a diagnostic flow-encoded gradient MR sequence that is to be subsequently executed;

a reconstruction processor provided with said different flow-encoded candidate raw datasets, said processor being configured to reconstruct flow-encoded image datasets respectively from said different flow-encoded candidate raw datasets;

a selection processor configured to select a flow-encoded candidate image dataset, from among said flow-encoded candidate image datasets, dependent on a background phase contrast established in a phase-contrast image assigned to one of said flow-encoded candidate image datasets; and a defining processor configured to define imaging sequence parameter values assigned to the selected flow-encoded candidate image dataset, as parameter values for said subsequent execution of said diagnostic flow-encoded magnetic resonance imaging, and to provide said parameter values for said diagnostic flow-encoded magnetic resonance imaging in an electronic form configured to operate said MR data acquisition scanner.

* * * * *